US00PP27281P3

(12) United States Plant Patent
Olesen et al.

(10) Patent No.: US PP27,281 P3
(45) Date of Patent: Oct. 18, 2016

(54) ***CLEMATIS* PLANT NAMED 'EVIPO027'**

(50) Latin Name: *Clematis viticella*
Varietal Denomination: Evipo027

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 131 days.

(21) Appl. No.: 14/121,290

(22) Filed: Aug. 15, 2014

(65) Prior Publication Data

US 2016/0050833 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

"Perfection by Poulsen—*Clematis* Main Varieties 2013" (3 pgs total).*

* cited by examiner

*Primary Examiner* — Susan McCormick Ewoldt

(57) ABSTRACT

A new *Clematis* plant with a compact growth habit, profuse, pink flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

1 Drawing Sheet

Botanical classification: Genus: *Clematis*. Species: *viticella*.

Variety denomination: 'Evipo027'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented varieties.

The two parents were crossed during the summer of 1997 and the resulting seeds were planted the following winter in a controlled environment in Guernsey, Channel Islands, United Kingdom. The new variety named 'Evipo027' originated as a single seedling from the stated cross.

The new *clematis* plant may be distinguished from its female seed parent and male pollen parent by the following characteristics. The female seed parent has flowers which are 120 mm in diameter, while the new plant has flowers which are 145 mm in diameter. The pollen parent starts to flower in May while the new plant flowers earlier, typically in April.

The objective of the hybridization of this *clematis* plant was to create a new and distinct variety for nursery culture with unique qualities such as:

1. Uniform and abundant pink flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo027' was selected by Mogens N. Olesen and Raymond J. Evison in their *clematis* development program in the Channel Islands, United Kingdom in 1998. Asexual reproduction of 'Evipo027' by means of vegetative cuttings and traditional layering was first performed by Mogens N. Olesen and Raymond J. Evison in the nursery during the summer of 1998. This initial and subsequent asexual propagations have demonstrated that the characteristics of 'Evipo027' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo027'.

Specifically illustrated in the drawing are flowers at various stages of development, flower in parts, leaves, and stems. Plants shown are 2 years of age.

DETAILED DESCRIPTION OF THE VARIETY

The following is a detailed description of 'Evipo027', as observed in its growth throughout the flowering period in open air culture in Yamhill County Oreg. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, physical characteristics of the *clematis* variety 'Evione' described and illustrated in U.S. Plant Pat. No. 10,222 issued Feb. 3, 1998 are compared to 'Evipo027' in Chart 1.

CHART 1

| | 'Evipo027' | 'Evione' |
|---|---|---|
| Flower diameter | 145 mm | 130 to 180 mm |
| General tonality of flower color | Red-Purple Group 70 B, blend of Red-Purple Group 71A and 71B central bar | Purple Group 76A with Red-Purple Group 71A central bar. |

Flower and Flower Bud

Blooming habit: Recurrent. The natural flowering period is generally from April to September.

Flower bud:

*Size*.—Normally 35 mm in length. Bud diameter is 17 mm.

*Bud form*.—Broad based. The base is rounded, apex is acute.

*Bud color*.—Yellow-Green Group 144B.

*Texture*.—Lightly pubescent.

Peduncle:

*Surface texture*.—Smooth.

*Length*.—25 to 45 mm.

*Width*.—2 mm.

*Color*.—Yellow-Green Group 144A.

*Strength*.—Strong.

Receptacle:

*Surface texture*.—Smooth.

*Shape*.—Funnel.

*Size*.—1 mm (h)×4 mm (w).

*Color*.—Yellow-Green Group 144A.

Flower arrangement:

*Location on vine*.—New and old growth.

*Borne*.—Singly, and from axillary buds borne at the base of the peduncle.

*Aspect*.—Flowers are oriented upwards.

*Overlapping*.—Somewhat.

Flower bloom:

*Size*.—On average, flowers are 145 mm in diameter and 20 mm in depth.

*Profile*.—Open flowers are flat on the upper surface, and concave underneath.

*Fragrance*.—None.

*Lasting quality*.—Flowers normally remain 6 days on the plant.

Tepals:

*Color, upper side*.—Red-Purple Group 70 B with a central bar which is a blend of Red-Purple Group 71A and 71B.

*Color, lower side*.—Red-Purple Group 76B with a central bar Yellow-Green Group 145C.

*Color, changes*.—After the flowers have been open for about 5 days, the upper surface becomes Red-Purple Group 75A with a central bar Red-Purple Group 77A. The lower surface becomes Red-Purple Group 76B with a central bar Green-White Group 157D.

*Quantity*.—Normally 6 to 8 tepals.

*Size*.—60 mm in length by 40 mm wide.

*Shape*.—Individual tepal shape is elliptic. The tepal apex is acute, the base is acute.

*Apex recurvature*.—Strong to moderate.

*Tepal cross section*.—Reflexed moderately.

*Margins*.—Entire. Strong undulations of margin observed.

*Persistence*.—Tepals drop off clean from the plant.

Reproductive organs:

*Arrangement*.—Open.

*Pollen*.—None observed.

*Anthers*.—Size: 5 mm in length. Color: Yellow Group 4D. Quantity: On average, 85.

*Filaments*.—Color: Green-White Group 157D. Length: 6 mm average.

*Pistils*.—Quantity: On average, 35.

*Stigmas*.—Superior in location relative to the length of the filaments and the height of the anthers.

*Styles*.—Color: Green-White Group 157D. Length: 11 mm.

Plant

Plant form: Climbing.

Plant growth: Moderately vigorous.

Size: Seasons growth attains 3 meters in height. Average spread is 45 cm.

Hardiness: Trials to date show the variety hardy in USDA Zones 4-9.

Stems:

*Color*.—Juvenile stems are Yellow-Green Group 144A. Mature stems are Greyed-Purple Group 183B.

*Internodes*.—On average, 6 cm between nodes.

*Length*.—Normally 20 cm from the base of the plant to the flowering portion of the stem.

*Diameter*.—Normally 2 mm.

*Texture*.—Mature stems are lightly pubescent and ribbed.

Plant foliage:

*Leaf characteristics*.—Deciduous, ternate.

*Arrangement*.—Trifoliate.

*Leaf size*.—Compound leaves are normally 120 mm (l)×110 mm (w). Leaflets are normally 55 mm (l)×35 mm (w).

*Abundance*.—On average 2 leaves per 10 cm of stem.

*Leaf color*.—Juvenile upper Yellow-Green Group 146A. Juvenile lower Yellow-Green Group 146B. Mature upper Yellow-Green Group 146A. Mature lower Yellow-Green Group 146B.

*Stipules*.—Absent.

*Petioles*.—Size: Normally 50 mm in length by 1 mm diameter. Texture: Lightly pubescent. Color: Yellow-Green Group 146B.

*Petiolule*.—Size: Normally 20 mm in length by 1 mm diameter. Texture: Smooth. Color: Yellow-Green Group 146B.

*Leaflet shape*.—Somewhat cordate. The apex is mucronate. The base is rounded.

*Margin*.—Entire, with moderate undulations.

*Surface*.—The upper side is smooth. The lower side is smooth.

*Thickness*.—Average.

*Glossiness*.—Glossy at the undersurface. Upper surface is not glossy.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo027', substantially as described and illustrated, due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

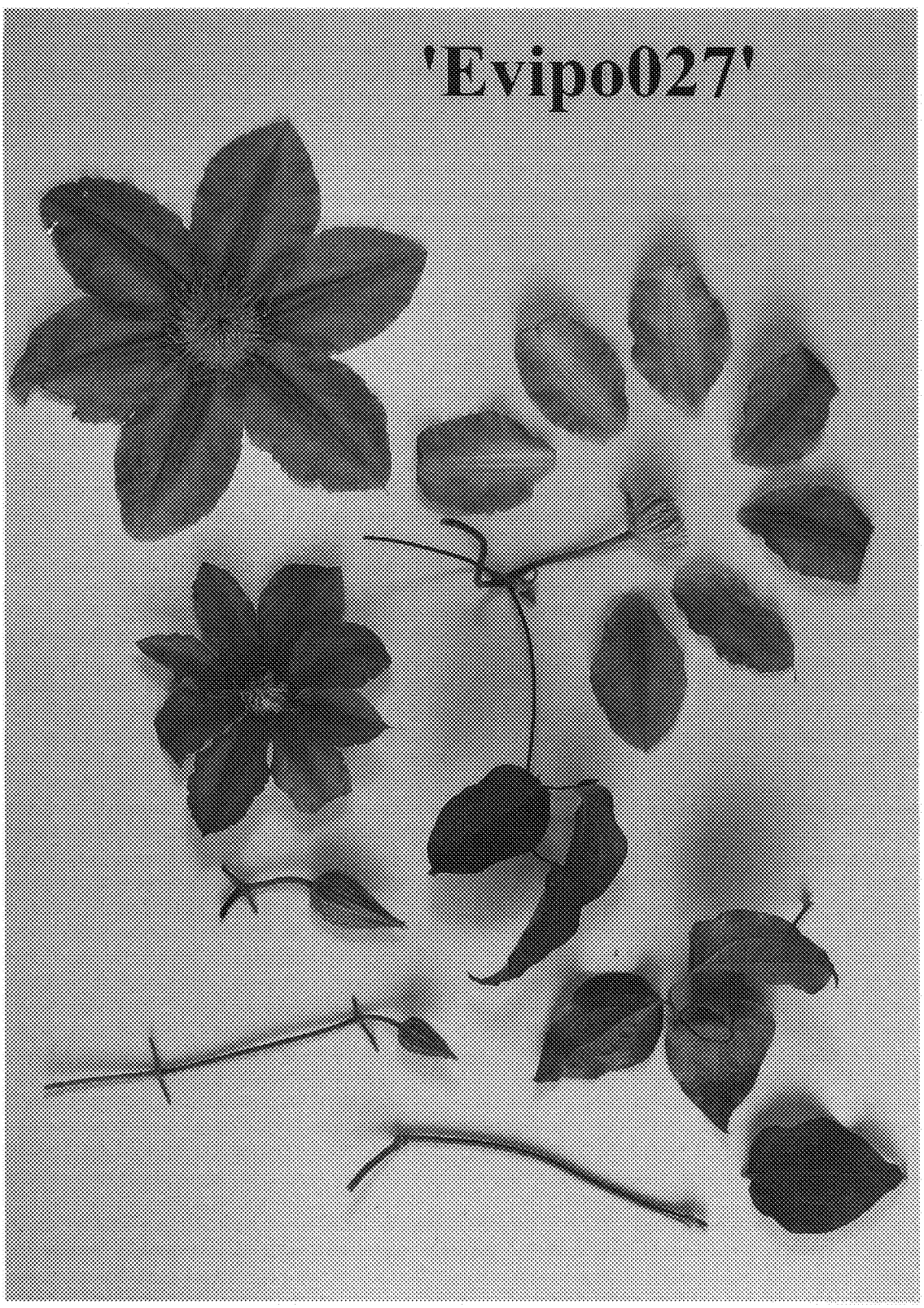
'Evipo027'